United States Patent [19]

Meyer et al.

[11] 4,360,466

[45] Nov. 23, 1982

[54] N'-[2,6-DICHLORO-4-(SUBSTITUTED-BENZYLIDENEAMINO)PHENYL]-N,N-DIMETHYLFORMAMIDINES

[75] Inventors: Walter E. Meyer, Suffern, N.Y.; Andrew S. Tomcufcik, Old Tappan, N.J.; Joseph W. Marsico, Jr., Pearl River, N.Y.

[73] Assignee: American Cyanamid Company, Stamford, Conn.

[21] Appl. No.: 325,069

[22] Filed: Nov. 25, 1981

[51] Int. Cl.³ .................. C07D 307/77; C07C 121/78; C07C 123/00
[52] U.S. Cl. .............................. 549/442; 260/465 E; 564/221; 564/245; 424/282; 424/304; 424/326; 549/437
[58] Field of Search .................. 260/465 E, 340.5; 564/245, 221; 424/326

[56] References Cited

U.S. PATENT DOCUMENTS

| | | | |
|---|---|---|---|
| 3,153,033 | 10/1964 | Steiger | 564/245 X |
| 3,855,292 | 12/1974 | Wollweber et al. | 564/245 X |
| 4,011,342 | 3/1977 | Schwartz et al. | 424/326 |

Primary Examiner—Dolph H. Torrence
Attorney, Agent, or Firm—Edward A. Conroy, Jr.

[57] ABSTRACT

This disclosure describes novel N'-[2,6-dichloro-4-(substituted-benzylideneamino)phenyl]-N,N-dimethylformamidines which possess activity as hypotensive agents and as diuretics.

12 Claims, No Drawings

N'-[2,6-DICHLORO-4-(SUBSTITUTED-BENZYLIDENEAMINO)PHENYL]-N,N-DIMETHYLFORMAMIDINES

BRIEF SUMMARY OF THE INVENTION

This invention relates to new organic compounds and, more particularly, is concerned with novel N'-[2,6-dichloro-4-(substituted-benzylideneamino)phenyl]-N,N-dimethylformamidines which may be represented by the following structural formula:

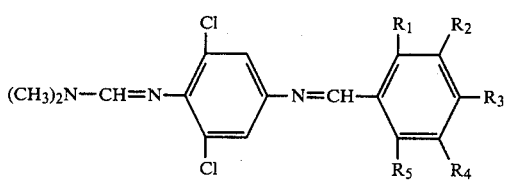

wherein $R_1$, $R_2$, $R_4$ and $R_5$ are each individually selected from the group consisting of hydrogen, fluoro, chloro, bromo, hydroxy, methoxy, methyl and trifluoromethyl; $R_3$ is selected from the group consisting of hydrogen, fluoro, chloro, bromo, cyano, hydroxy, methoxy, methyl, trifluoromethyl, phenyl, acetamido, dimethylamino and diethylamino; and $R_2$ and $R_3$ taken together is methylenedioxy with the proviso that at least two of $R_1$, $R_2$, $R_3$, $R_4$ and $R_5$ are hydrogen. A preferred embodiment of the present invention may be represented by the above structural formula wherein $R_1$ and $R_2$ may be the same or different and are hydrogen, fluoro, chloro, bromo, hydroxy, methoxy or methyl, $R_4$ and $R_5$ may be the same or different and are hydrogen, chloro, methoxy or methyl, and $R_3$ is hydrogen, bromo, cyano, methoxy, phenyl, dimethylamino or diethylamino with the proviso that at least two of $R_1$, $R_2$, $R_3$, $R_4$ and $R_5$ are hydrogen.

The organic bases of this invention form non-toxic acid-addition salts with a variety of pharmacologically acceptable organic and inorganic salt-forming reagents. Thus, acid-addition salts, formed by a mixture of the organic free base with one or more equivalents of an acid, suitably in a neutral solvent, are formed with such acids as sulfuric, phosphoric, hydrochloric, hydrobromic, sulfamic, citric, lactic, malic, succinic, tartaric, acetic, benzoic, gluconic, ascorbic, and the like. For purposes of this invention the free bases are equivalent to their non-toxic acid-addition salts. The acid-addition salts of the organic bases of the present invention are, in general, crystalline solids, relatively soluble in water, methanol and ethanol but relatively insoluble in non-polar organic solvents such as diethyl ether, benzene, toluene, and the like.

DETAILED DESCRIPTION OF THE INVENTION

The novel compounds of the present invention may be readily prepared as set forth in the following reaction scheme:

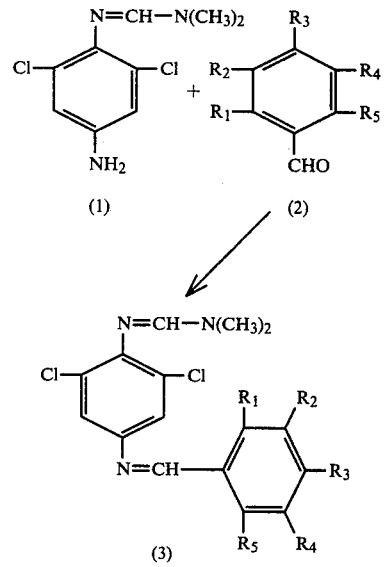

wherein $R_1$, $R_2$, $R_3$, $R_4$ and $R_5$ are as hereinabove defined. In accordance with the above reaction scheme, N'-(2,6-dichloro-4-aminophenyl)-N,N-dimethylformamidine (1) is dissolved in an inert solvent such as ethanol and treated at ambient temperature or at the reflux temperature for one to 18 hours with or without the removal of water with a benzaldehyde of the general structure (2) to yield the N,N-dimethyl-N'-(4-benzylideneaminophenyl)formamidine compounds (3) of the instant invention. These products may be purified by crystallization from common solvents such as ethanol or combinations of solvents such as ethanol and n-hexane.

Alternatively, the novel compounds of the present invention may be prepared as set forth in the following reaction scheme:

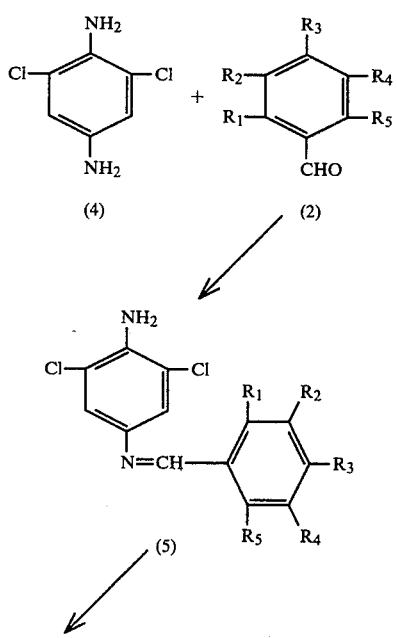

-continued

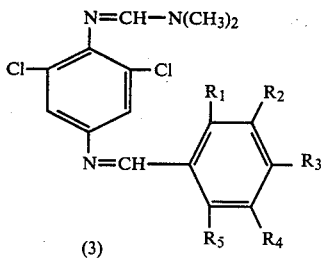

(3)

wherein $R_1$, $R_2$, $R_3$, $R_4$ and $R_5$ are as hereinabove defined. In accordance with the above reaction scheme, 2,6-dichloro-p-phenylenediamine (4) is dissolved in an inert solvent such as ethanol and treated at ambient temperature or at the reflux temperature for one to 18 hours with or without the removal of water with a benzaldehyde of the general structure (2) to yield the intermediate 2,6-dichloro-$N^4$-benzylidene-p-phenylenediamine compounds (5). Treatment of (5) with a formamidine forming reagent such as N,N-dimethylformamide dimethylacetal neat, or in an inert solvent by heating, usually at the reflux temperature, for from 4 to 30 hours provides the compounds (3) of the instant invention. After evaporation of the solvents, the products can be purified by crystallization from usual solvents such as ethanol or a combination of solvents such as ethanol and n-hexane.

The novel compounds of the present invention are physiologically active and, therefore, useful in the pharmaceutical field. In particular, these compounds are useful as either diuretic and/or hypotensive agents.

The novel compounds of the present invention are potent diuretics, producing significant water diuresis and sodium ($Na^+$) loss, but with minimal loss of potassium ($K^+$), as determined in the following procedure.

One to three spontaneously hypertensive rats are dosed by gavage with a test compound at one to 100 mg./kg. of body weight and loaded with 0.9% sodium chloride at 25 ml./kg. of body weight at zero hour. The 0-5 hour urine is collected, its volume measured, and $Na^+$ and $K^+$ concentrations determined. The following compounds have been found to possess significant diuretic activity when tested as described above:

N'-[2,6-Dichloro-4-(2,6-dichlorobenzylideneamino)-phenyl]-N,N-dimethylformamidine
N'-[2,6-Dichloro-4-(2,6-dimethylbenzylideneamino)-phenyl]-N,N-dimethylformamidine.
N'-[2,6-Dichloro-4-[(2-chloro-4-dimethylaminobenzylideneamino)phenyl]-N,N-dimethylformamidine
N'-[2,6-Dichloro-4-(3,4,5-trimethoxybenzylideneamino)phenyl]-N,N-dimethylformamidine cpd with methanol
N'-[2,6-Dichloro-4-(3,5-dimethoxybenzylideneamino)phenyl]-N,N-dimethylformamidine
N'-[2,6-Dichloro-4-(p-cyanobenzylideneamino)-phenyl]-N,N-dimethylformamidine
N'-(2,6-Dichloro-4-piperonylideneaminophenyl)-N,N-dimethylformamidine
N'-[2,6-Dichloro-4-(p-diethylaminobenzylideneamino)phenyl]-N,N-dimethylformamidine
N'-[2,6-Dichloro-4-(3-fluoro-4-methoxybenzylideneamino)-phenyl]]-N,N-dimethylformamidine
N'-[2,6-Dichloro-4-(m-fluorobenzylideneamino)-phenyl]-N,N-dimethylformamidine
N'-[2,6-Dichloro-4-(o-hydroxybenzylideneamino)-phenyl]-N,N-dimethylformamdine
N'-[2,6-Dichloro-4-[(m-trifluoromethyl)benzylideneamino]-phenyl]-N,N-dimethylformamidine
N'-[2,6-Dichloro-4-(o-fluorobenzylideneamino)-phenyl]-N,N-dimethylformamidine
N'-[2,6-Dichloro-4-(3,5-dichlorobenzylideneamino)-phenyl]-N,N-dimethylformamidine
N'-[2,6-Dichloro-4-(p-phenylbenzylideneamino)-phenyl]-N,N-dimethylformamidine
4'-[N-[3,5-Dichloro-4-(dimethylaminomethyleneaminophenyl]-formimidoyl]acetanilide
N'-[4-(p-Bromobenzylideneamino)-2,6-dichlorophenyl]-N,N-dimethylformamidine
N'-[4-(m-Bromobenzylideneamino)-2,6-dichlorophenyl]-N,N-dimethylformamidine
N'-[2,6-Dichloro-4-(p-dimethylaminobenzylideneamino)phenyl]-N,N-dimethylformamidine
N'-[2,6-Dichloro-4-(4-dimethylamino-2-methoxybenzylideneamino)phenyl]-N,N-dimethylformamidine
4'-[N-[3,6-Dichloro-4-(dimethylaminomethyleneamino)phenyl]-formimidoyl]-3,4,5-trimethoxybenzanilide
N'-[2,6-Dichloro-4-(4-diethylaminosalicylideneamino)phenyl]-N,N-dimethylformamidine
N'-[2,6-Dichloro-4-(4-dimethylaminosalicylideneamino)phenyl]-N,N-dimethylformamidine
N'-[4-(3-Bromo-4-dimethylaminobenzylideneamino)-2,6-dichlorophenyl]-N,N-dimethylformamidine
N'-[2,6-Dichloro-4-(p-dimethylaminocinnamylideneamino)phenyl]-N,N-dimethylformamidine
N'-[2,6-Dichloro-4-(4-dimethylamino-2-methylbenzylideneamino)phenyl]-N,N-dimethylformamidine
N'-[4-(2-Bromo-4-dimethylaminobenzylideneamino)-2,6-dichlorophenyl]-N,N-dimethylformamidine
N'-[2,6-Dichloro-4-(4-dimethylamino-2-fluorobenzylideneamino)phenyl]-N,N-dimethylformamidine
N'-[2,6-Dichloro-4-(2-chloro-4-methoxybenzylideneamino)-phenyl]-N,N-dimethylformamidine The novel compounds of the present invention also possess anti-hypertensive activity of non-toxic doses and as such as useful as hypotensive agents. The hypotensive properties of the compounds of the present invention have been shown when orally administered to mammals, specifically warm-blooded animals as described below.

The novel compounds of the present invention were tested for anti-hypertensive activity in a procedure using spontaneously hypertensive rats (SHR) as follows: One male adult SHR (16-20 weeks old) weighing about 300 grams (Taconic Farms, Germantown, N.Y.) is dosed by gavage with the test compound at one to 100 mg./kg. with 0.9% sodium chloride loading at 25 ml./kg. at zero hour. A second identical dose is given at 24 hours without saline loading and the mean arterial blood pressure (MABP) of the conscious rat is measured directly by femoral artery puncture at 28 hours. A 2nd or 3rd SHR rat may be needed depending on the results of the 1st rat [Chan, et al., Pharmacologist, 17, 253 (1975)]. The following representative compounds of the present invention have been shown to possess anti-hypertensive activity when tested as described above.

N'-[2,6-Dichloro-4-(2,6-dichlorobenzylideneamino-phenyl]-N,N-dimethylformamidine
N'-[2,6-Dichloro-4-(2,6-dimethylbenzylideneamino-phenyl]-N,N-dimethylformamidine
N'-[2,6-Dichloro-4-(2-chloro-4-dimethylaminobenzylideneamino)phenyl]-N,N-dimethylformamidine
N'-[2,6-Dichloro-4-(3,4,5-trimethoxybenzylideneamino)phenyl]-N,N-dimethylformamidine cpd with methanol
N'-[2,6-Dichloro-4-(3,5-dimethoxybenzylideneamino)phenyl]-N,N-dimethylformamidine
N'-[2,6-Dichloro-4-(p-cyanobenzylideneamino)-phenyl]-N,N-dimethylformamidine
N'-(2,6-Dichloro-4-piperonylideneaminophenyl)-N,N-dimethyl formamidine
N'-[2,6-Dichloro-4-(p-diethylaminobenzylideneamino)phenyl]-N,N-dimethylformamidine
N'-[2,6-Dichloro-4-(3-fluoro-4-methoxybenzylideneamino)phenyl]-N,N-dimethylformamidine
N'-[2,6-Dichloro-4-(m-fluorobenzylideneamino)-phenyl]-N,N-dimethylformamidine
N'-[2,6-Dichloro-4-(o-hydroxybenzylideneamino)-phenyl]-N, N-dimethylformamidine
N'-[2,6-Dichloro-4-[[m-(trifluoromethyl)benzylideneamino]-phenyl]-N,N-dimethylformamidine
N'-[2,6-Dichloro-4-(o-fluorobenzylideneamino)-phenyl]-N,N-dimethylformamidine
N'-[2,6-Dichloro-4-(3,5-dichlorobenzylideneamino)-phenyl]-N,N-dimethylformamidine
N'-[2,6-Dichloro-4-(p-phenylbenzylideneamino)-phenyl]-N,N-dimethylformamidine
4'-[N-[3,5-Dichloro-4-(dimethylaminomethyleneamino)phenyl]formimidoyl]acetanilide
N'-[4-(p-Bromobenzylideneamino)-2,6-dichloro-phenyl]-N,N-dimethylformamidine
N'-[4-(m-Bromobenzylideneamino)-2,6-dichloro-phenyl]-N,N-dimethylformamidine
N'-[2,6-Dichloro-4-(p-dimethylaminobenzylideneamino)phenyl]-N,N-dimethylformamidine
N'-[2,6-Dichloro-4-(4-dimethylaminosalicylideneamino)phenyl]-N,N-dimethylformamidine
N'-[4-(3-Bromo-4-dimethylaminobenzylideneamino)-2,6-dichlorophenyl]-N,N-dimethylformamidine
N'-[2,6-Dichloro-4-(p-dimethylaminocinnamylideneamino)phenyl]-N,N-dimethylformamidine
N'-[4-(2-Bromo-4-dimethylaminobenzylideneamino)-2,6-dichlorophenyl]-N,N-dimethylformamidine
N'-[2,6-Dichloro-4-(4-dimethylamino-2-fluorobenzylideneamino)phenyl]N,N-dimethylformamidine The novel compounds of the present invention have thus been shown to be valuable diuretic agents of low toxicity when administered orally. The amount of a single dose or of a daily dose will vary but should be such as to give a proportionate dosage of from about one mg. to about 1000 mg. per day for a subject of about 70 kg. body weight. The dosage regimen may be adjusted to provide the optimum therapeutic response, for example, doses of 25–250 mg. may be administered on a four times per day regimen, or the dose may be proportionately increased as indicated by the exigencies of the therapeutic situation.

The novel compounds of the present invention have also been found to be highly useful or lowering elevated blood pressure to mammals when administered in amounts ranging from about 0.4 mg. to about 10.0 mg. per kg. of body weight per day. A preferred dosage regimen for optimum results would be from about 7.0 mg. to about 175 mg. per dose. Such dosage units are employed that a total of from about 28 mg. to about 700 mg. of active compound for a subject of about 70 kg. of body weight are administered in a 24 hour period. The dosage regimen may be adjusted to provide the optimum therapeutic response. For example, several divided doses may be administered daily or the dose may be proportionally reduced as indicated by the exigencies of the therapeutic situation. The compounds of of this invention are preferably administered orally but may be administered in any convenient manner such as the intravenous route.

The compounds of the present invention may be administered as active components of compositions in unit dosage form such as tablets, pills, capsules, powders, granules, oral or parenteral solutions or suspensions and the like. For preparing solid compositions such as tablets, the active compound is mixed with conventonal tableting ingredients such as starch, lactose, sucrose, sorbitol, talc, stearic acid, magnesium stearate, dicalcium phosphate, gums and functionally similar materials as pharmaceutical diluents or carriers. The tablets or pills can be laminated or otherwise compounded to provide a dosage form affording the advantage of prolonged or delayed action, or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids of mixtures of polymeric acids with such material as shellac and cetyl alcohol, cellulose acetate, and the like. A particularly advantageous enteric coating comprises a styrene maleic acid copolymer together with known materials contributing to the enteric properties of the coating.

Compositions according to the present invention having the desired clarity, stability and adaptability for parenteral use are obtained by dissolving from 0.10% to 10% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10 to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorphenyl-α-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

The novel compounds of the present invention are adapted to intravenous administration when diluted with water or diluents employed in intravenous therapy such as isotonic glucose in appropriate quantities. For intravenous use, initial concentrations down to about 0.05 to 0.25 mg./ml. of active ingredient are satisfactory.

The liquid forms in which the compounds of the present invention may be incorporated for administration include aqueous solutions, suitably flavored syrups, aqueous or oil suspensions, flavored emulsions with edible oils such as cottonseed oil, sesame oil, coconut oil, peanut oil, and the like, as well as elixirs and similar pharmaceutical vehicles. Suitable dispersing or suspending agents for aqueous suspensions include synthetic and and natural gums such as tragacanth, acacia, alginic acid, dextran, sodium carboxymethylcellulose, methylcellulose, polyvinylpyrrolidone, gelatin and the like.

The term unit dosage form refers to physically discrete units suitable as unitary dosages, each unit containing a predetermined quantity of active material calculated to produce the desired therapeutic effect in association with the required pharmaceutical diluent, carrier or vehicle. The specifications for the unit dosage forms of this invention are dictated by and are directly dependent on (a) the unique characteristic of the active material and the particular therapeutic effect to be achieved, and (b) the limitations inherent in the art of compounding such an active material for therapeutic use, as disclosed in detail in this specification, these being features of the present invention.

The invention will be described in greater detail in conjunction with the following specific examples.

EXAMPLE 1

N'-[2,6-Dichloro-4-(2,6-dichlorobenzylideneamino)-phenyl]-N,N-dimethylformamidine To a boiling solution of 8.85 g. of 2,6-dichloro -p-phenylenediamine in 250 ml. of absolute ethanol is added 8.75 g. of 2,6-dichlorobenzaldehyde. The solution is boiled for 10 minutes longer and set aside to cool. The cooled solution is filtered to provide 13.8 g. of yellow-tan crystals. The product is washed with absolute ethanol and air dried. The filtrate is concentrated to ½ volume, and allowed to stand, then is filtered to provide an additional 1.54 g. of 2,6-dichloro-$N^4$-2,6-dichlorobenzylidene-p-phenylenediamine, m.p. 136°–138° C.

A mixture of 5.01 g. of the preceding product and 40 ml. of N,N-dimethylformamide dimethylacetal is heated under reflux at 125° C. for 4 hours. The mixture is cooled and evaporated in vacuo to give a green, gummy residue which crystallizes on standing. The residue is recrystallized twice from ethyl acetate-petroleum ether (35°–60° C.) to yield 1.53 g. of the desired product as light brown crystals, m.p. 84°–86° C.

EXAMPLE 2

N'-[2,6-Dichloro-4-(2,6-dimethylbenzylideneamino)-phenyl]-N,N-dimethylformamidine A mixture of 7.3 g. of 2,6-dimethylbenzaldehyde (Org. Sym. Coll., Vol, III, p. 551) and 9.6 g. of 2,6-dichlorophenylenediamine in 200 ml. of ethanol is refluxed for 18 hours. The solvent is evaporated and the residue is dissolved in 150 ml. of hot methanol, treated with activated charcoal and filtered through diatomaceous earth. The product is precipitated on standing as fine needles. The material is collected by filtration, washed with methanol followed by ether to give 1.0 g. of 2,6-dichloro-$N^4$-2,6-dimethylbenzylidene-p-phenylenediamine as dark yellow crystals, m.p. 123°–124° C.

A 2.6 g. amount of the preceding product (prepared as described) and 10 ml. of N,N-dimethylformamide dimethylacetal is heated at reflux for 2 hours. The resulting dark solution is evaporated to afford an oil which crystallizes on standing. This material is recrystallized from ethanol, collected by filtration and washed with methanol to yield 2.0 g. of the product of the Example as pale yellow needles, m.p. 118°–119° C.

EXAMPLE 3

N'-[2,6-Dichloro-4-(2-chloro-4-dimethylaminobenzylideneamino)phenyl]-N,N-dimethylformamidine A mixture of 18.3 g. of 2-chloro-4-dimethylaminobenzaldehyde and 17.7 g. of 2,6-dichlorophenylenediamine in 200 ml. of ethanol is refluxed for 18 hours. The reaction mixture is evaporated to dryness. The residue is dissolved in 1400 ml. of boiling ethanol, treated with activated charcoal and filtered through diatomaceous earth. The filtrate is evaporated to 600 ml. and 200 ml. of water is added. The mixture is cooled, the precipitated product is collected by filtration, washed with ethanol/water and air dried. The mustard colored crystals are redissolved in 800 ml. of ethanol and evaporated to 600 ml. by boiling. Then 100 ml. of water is added and the mixture is allowed to stand for 16 hours in a chill room at 5° C. The product is collected by filtration and washed with ethanol/water then dried to give 3.7 g. of 2,6-dichloro-$N^4$-(2-chloro-4-dimethylaminobenzylidene)-p-phenylenediamine as mustard colored crystals, m.p. 139°–140° C.

A 7.0 g. amount of the above compound in 25 ml. of N,N-dimethylformamide dimethylacetal is refluxed for 3 hours. The reaction mixture is concentrated to a syrup in vacuo and ethanol is added to crystallize the product. The product is collected by filtration and washed with ether to give 7.3 g. of the product of the Example as dark yellow crystals, m.p. 130°–131° C.

EXAMPLE 4

N'-[2,6-Dichloro-4-(3,4,5-trimethoxybenzylideneamino) phenyl]-N,N-dimethylformamidine compound with methanol A mixture of 5.3 g. of 2,6-dichlorophenylenediamine and 5.9 g. of 3,4,5-trimethoxybenzaldehyde is refluxed for 2 hours to provide yellow granular crystals. The reaction mixture is cooled and filtered. The product is washed with a small amount of ethanol to yield 9.0 g. of 2,6-dichloro-$N^4$-(3,4,5-trimethoxybenzylidine)-p-phenylenediamine, m.p. 148°–150° C.

A 5.0 g. amount of the above product in 20 ml. of N,N-dimethylformamide dimethylacetal is refluxed for 18 hours. The reaction solution is evaporated to an amber syrup which is dissolved in 20 ml. of methanol and cooled at 5° C. The precipitate formed is collected by filtration and washed with methanol to provide 6.1 g. of the desired product as pale yellow crystals, m.p. 86°-88° C.

EXAMPLE 5

N'-[2,6-Dichloro-4-(3,5-dimethoxybenzylideneamino)-phenyl]-N,N-dimethylformamidine A mixture of 11.7 g. of 2,6-dichlorophenylenediamine and 10.8 g. of 3,5-dimethoxybenzaldehyde in 200 ml. of absolute ethanol is refluxed for 4 hours to yield crystals. The product is collected and washed with ethanol to provide 18.7 g. of 2,6-dichloro-$N^4$-(3,5-dimethoxybenzylideneamino)-p-phenylenediamine as light tan needles, m.p. 133°-135° C.

A 5.1 g. portion of the preceding product and 20.0 ml. of N,N-dimethylformamide dimethylacetal is refluxed for 2.5 hours. The resulting solution is evaporated to an amber syrup. The syrup is treated with ethanol to crystallize the product as dark amber rods. The material is collected and washed with ethanol then is recrystallized from ethanol to yield 4.7 g. of the product of the Example as dark yellow granules, m.p. 120.5°-121.5° C.

EXAMPLE 6

N'-[2,6-Dichloro-4-(p-cyanobenzylideneamino)phenyl]-N,N-dimethylformamidine

A 5.3 g. amount of 2,6-dichlorophenylenediamine is dissolved in 50 ml. of warm methanol and is poured into a solution of 3.9 g. of p-cyanobenzaldehyde with the immediate precipitation of yellow crystals. The mixture is allowed to stand at room temperature for 16 hours. The precipitate is slurried with methanol, collected by filtration and washed with methanol to yield 6.0 g. of p-[N-(4-amino-3,5-dichlorophenyl)formimidoyl]]benzonitrile as light yellow crystals, m.p. 169°-170° C.

A 3.0 g. amount of the preceding compound and 20 ml. of N,N-dimethylformamide dimethylacetal is refluxed for 18 hours. The mixture is cooled. The precipitate is collected by filtration and washed with cold methanol to provide 3.6 g. of the product of the Example as yellow crystals, m.p. 193°-195° C.

EXAMPLE 7

N'-[2,6-Dichloro-4-(piperonylideneamino)phenyl]-N,N-dimethylformamidine

A mixture of 7.1 g. of recrystallized 2,6-dichloro-p-phenylenediamine, 6.0 g. of piperonal and 100 ml. of absolute ethanol is refluxed for 18 hours in a 300 ml. round bottom flask. The reaction mixture is allowed to stand for 16 hours then is cooled at 5° C. for 30 minutes. The crystalline product is collected by filtration and washed with cold ethanol, then ether to give 9.4 g. of 3,5-dichloro-$N^4$-piperonylidene-p-phenylenediamine as yellow-tan crystals, m.p. 134°-135° C.

A mixture of 3.19 g. of the preceding product and 15 ml. of N,N-dimethylformamide dimethylacetal is refluxed for 18 hours. The solvent is evaporated and the yellow solid is dissolved in 150 ml. of boiling methanol. The solution is filtered and the filtrate is cooled at 5° C. The precipitate formed is collected by filtration to give 2.2 g. of the desired product as shiny yellow plates, m.p. 155°-156° C.

EXAMPLE 8

N'-[2,6-Dichloro-4-[(p-diethylaminobenzylideneamino)phenyl]-N,N-dimethylformamidine A 10.8 amount of recrystallized 2,6-dichloro-p-phenylenediamine is dissolved in 75 ml. of warm ethanol, then 10.8 g. of p-diethylaminobenzaldehyde is added and the mixture is refluxed for 18 hours. The reaction mixture is diluted to one liter with n-hexane. The solution is evaporated to a dark amber syrup. The syrup forms crystals in the presence of toluene. Hexane is added and the crystals are collected by filtration and washed with hexane. The filtrate and wash are combined and evaporated in vacuo to give 3.7 g. of 2,6-dichloro-$N^4$-(p-diethylaminobenzylidene)-p-phenylenediamine as light yellow crystals, m.p. 56°-57° C.

The preceding compound (3.7 g.) in 10 ml. of N,N-dimethylformamide dimethylacetal is refluxed for 8 hours. The reaction mixture is allowed to stand at room temperature for 18 hours, then is evaporated to an amber syrup. Ethanol (15 ml) is added to the syrup to form crystals. The product is collected by filtration, washed with ethanol/hexane then hexane to give 3.4 g. of the product of the Example as bright yellow crystals, m.p. 118°-119° C.

EXAMPLE 9

N'-[2,6-Dichloro-4-(3-fluoro-4-methoxybenzylideneamino)phenyl]-N,N-dimethylformamidine A mixture of 20.7 g. of 2,6-dichloro-p-nitroaniline and 15 ml. of N,N-dimethylformamide dimethylacetal in 125 ml. of dimethylformamide is heated on a steam bath for 4 hours. The reaction mixture is cooled at −10° C. and the precipitate is collected by filtration. The product is washed and isopropyl alcohol and dried to give 21.5 g. of N'-(2,6-dichloro-4-nitrophenyl)-N,N-dimethylformamidine, m.p. 164°-166° C.

A 540 g. amount of stannous chloride is dissolved in 450 ml. of concentrated hydrochloric acid with stirring. The solution is cooled to 10° C. in an ice bath and 155 g. of N'-(2,6-dichloro-4-nitrophenyl)-N,N-dimethylformamidine (prepared as described above) is added portionwise, with stirring, at a rate to maintain the reaction temperature at 75° C. The reaction mixture is allowed to stand at room temperature for 18 hours, then is filtered. The filter cake is suspended in 200 ml. of ice water and concentrated sodium hydroxide is added until the reaction mixture is alkaline. The reaction mixture is filtered and the insolubles are collected and extracted with chloroform. The chloroform extracts are evaporated in vacuo to yield 102 g. of N'-(4-amino-2,6-dichlorophenyl)-N,N-dimethylformamidine as pale yellow crystals, m.p. 121°-126° C.

A 7.0 g. amount of N'-(4-amino-2,6-dichlorophenyl)-N,N-dimethylformamidine and 4.6 g. of 3-fluoro-p-anisaldehyde are each dissolved separately in 25 ml. of warm methanol and then combined. The mixture is cooled at 5° C. The crystallized product is collected and washed with ether to provide 8.2 g. of the product of the Example as yellow crystals, m.p. 139°-141° C.

EXAMPLE 10

N'-[2,6-Dichloro-4-(m-fluorobenzylideneamino)-phenyl]N,N-dimethylformamidine

A 7.0 g. amount of N'-(4-amino-2,6-dichlorophenyl)-N,N-dimethylformamidine (Example 9) is dissolved in 25 ml. of absolute ethanol then 3.7 g. of m-fluorobenzaldehyde is added and the mixture is refluxed for one hour. The solution is evaporated to an amber syrup which crystallizes. The material is dissolved in 50 ml. of refluxing ether and hexane is added until turbidity results. The crystalline product is collected and washed with hexane. The product is recrystallized from ether/hexane to give 1.4 g. of the product of the Example as hard yellow crystals, m.p. 95°–96° C.

EXAMPLE 11

N'-[2,6-Dichloro-4-(o-hydroxybenzylideneamino)-phenyl]N,N-dimethylformamidine

A mixture of 3.7 g. of salicylaldehyde and 7.0 g. of N'-[4-amino-2,6-dichlorophenyl]-N,N-dimethylformamidine is heated neat at 80° C. for 18 hours. The mixture is cooled and ethanol is added to give crystals. The mixture is heated and then cooled to recrystallize the product. The product is collected, washed with cold ethanol then ether to give 9.0 g. of the product of the Example as yellow crystals, m.p. 113°–115° C.

EXAMPLE 12

N'-[2,6-Dichloro-4-[[m-(trifluoromethyl)benzylidene]-amino]phenyl]-N,N-dimethylformamidine A mixture of 9.3 g. of N'-(4-amino-2,6-dichlorophenyl)-N,N-dimethylformamidine (Example 9) and 6.9 g. of m-trifluoromethylbenzaldehyde in 25 ml. of absolute ethanol is refluxed for 18 hours. The solution is evaporated in vacuo to give a syrup. The syrup is extracted into hot heptane. The solvent is evaporated to provide an oil. The oil is dissolved in chloroform and the solution is filtered through a magnesium silicate column packed with chloroform. The column is washed with chloroform until the wash is colorless. The filtrate is evaporated to give a yellow syrup which crystallizes on cooling. The product is recrystallized from n-hexane to give 8.3 g. of the product of the Example as granular yellow crystals, m.p. 62°–64° C.

EXAMPLE 13

N'-[2,6-Dichloro-4-(o-fluorobenzylideneamino)-phenyl]-N,N-dimethylformamidine

A mixture of 9.3 g. of N'-(4-amino-2,6-dichlorophenyl)-N,N-dimethylformamidine (Example 9) and 5.0 g. of o-fluorobenzaldehyde in 25 ml. of absolute ethanol is refluxed for 18 hours. The solution is evaporated in vacuo to provide a syrup. The syrup is dissolved in 50 ml. of ether and n-hexane is added to 500 ml. The solution is cooled and filtered. The filtrate is evaporated to 100 ml. to precipitate the product. The product is collected by filtration and washed with n-hexane to give 7.4 g. of the desired product as bright yellow crystals, m.p. 79°–81° C.

EXAMPLE 14

N'-[2,6-Dichloro-4-(3,5-dichlorobenzylideneamino)-phenyl]-N,N-dimethylformamidine A mixture of 13.3 g. of recrystallized 2,6-dichloro-p-phenylenediamine and 13.1 g. of 3,5-dichlorobenzaldehyde in 100 ml. of absolute ethanol is refluxed for 18 hours. The mixture is cooled and hexane is added. The product is collected by filtration and is washed with hexane until the wash is clear to give 24.3 g. of 2,6-dichloro-N⁴-3,5-dichlorobenzylidene-p-phenylenediamine as mustard colored crystals, m.p. 194°–195° C.

A 6.9 amount of the preceding compound in 25 ml. of N,N-dimethylformamide dimethylacetal is refluxed for 18 hours. The solvent is removed in vacuo and the residue is dissolved in 600 ml. of refluxing ethanol. The solvent is evaporated to 200 ml. by boiling. The mixture is cooled and the granular product is collected by filtration and washed with n-hexane to give 7.0 g. of the product of the Example as dark yellow crystals, m.p. 161°–162° C.

EXAMPLE 15

N'-[2,6-Dichloro-4-(p-phenylbenzylideneamino)-phenyl]N,N-dimethylformamidine

A 17.7 g. amount of sublimed and crystallized 2,6-dichloro-1,4-phenylenediamine is dissolved in 50 ml. of refluxing ethanol and 18.2 g. of 4-biphenylcarboxaldehyde is dissolved in 15 ml. of hot ethanol and added to the above solution and washed with an additional 10 ml. of hot ethanol. The orange-yellow solution is refluxed for 18 hours, then is cooled and filtered with cold ethanol. The product is washed with n-hexane to provide 35.0 g. of 2,6-dichloro-N⁴-p-phenylbenzylidene-p-phenylenediamine as bright yellow needles, m.p. 108°–110° C.

A 5.5 g. amount of the preceding compound in 20 ml. of N,N-dimethylformamide dimethylacetal is refluxed for 18 hours. The reaction mixture is evaporated in vacuo to give a syrup. The syrup is dissolved in ethanol to crystallize a product. The product is collected and washed with cold ethanol. The material is recrystallized from ethanol, collected and washed with n-hexane to give 4.8 g. of the product of the Example as bright yellow crystals, m.p. 124°–125° C.

EXAMPLE 16

4'-[N-[3,5-Dichloro-4-(dimethylaminomethyleneamino)-phenyl]formimidoyl]acetanilide A mixture of 3.5 g. of 2,6-dichloro-1,4-phenylenediamine and 3.3 g. of p-acetamidobenzaldehyde in 50 ml. of ethanol is refluxed for 2½ hours. The reaction mixture is allowed to stand at room temperature for 16 hours, then evaporated in vacuo to give a solid. The solid in 25 ml. of N,N-dimethylformamide dimethylacetal is refluxed for 18 hours. The solvent is evaporated to provide a syrup which is dissolved in ethanol and n-hexane. The addition of more ethanol provides crystals. The crude product is collected, dissolved in 50 ml. of hot ethanol and filtered through diatomaceous earth. The filter is washed with ethanol and n-hexane is added to the filtrate until turbid. The clear liquid is decanted and evaporated in vacuo to give hard, yellow-orange crystals. The material is recrystallized from ethyl acetate/hexane to give 830 mg. of the product of the Example as bright yellow crystals, m.p. 171°–173° C.

EXAMPLE 17

N'-[4-(p-Bromobenzylideneamino)-2,6-dichlorophenyl]-N,N-dimethylformamidine

A mixture of 9.2 g. of p-bromobenzaldehyde, 9.5 g. of recrystallized 2,6-dichloro-1,4-phenylenediamine and 50 ml. of absolute ethanol is refluxed for 2 hours. The reaction mixture is cooled and n-hexane is added. The precipitate is collected and washed with n-hexane until the wash is clear to give 10.3 g. of golden crystals. A 1.3 g. amount of the above material is recrystallized from ethanol. The product is filtered and washed with n-hexane to give 680 mg. of $N^4$-p-bromobenzylidene-2,6-dichloro-p-phenylenediamine as crystals, m.p. 146°–147° C.

A 3.0 g. amount of $N^4$-p-bromobenzylidene-2,6-dichloro-p-phenylenediamine (prepared as described above) and 15 ml. of N,N-dimethylformamide dimethylacetal is refluxed for 5 hours. The mixture is evaporated in vacuo to yield an amber syrup. The syrup is dissolved in ethanol and n-hexane is added to crystallize a product. The material is collected by filtration and washed with n-hexane to give 2.8 g. of the product of the Example as golden granular rods, m.p. 134°–136° C.

EXAMPLE 18

N'-[4-(m-Bromobenzylideneamino)-2,6-dichlorophenyl]-N,N-dimethylformamidine

A 17.7 g. amount of recrystallized 2,6-dichloro-1,4-phenylenediamine is dissolved in 50 ml. of absolute ethanol, then 18.5 g. of m-bromobenzaldehyde is added. Crystallization of a product takes place within one minute, then n-hexane is added. The product is collected by filtration to give 31.0 g. of $N^4$-m-bromobenzylidene-2,6-dichloro-p-phenylenediamine as pale yellow crystals, m.p. 136°–138° C.

A mixture of 6.9 g. of the preceding compound and 25 ml. of N,N-dimethylformamide dimethylacetal is refluxed for 18 hours. The resulting pale yellow solution is evaporated to a yellow syrup. The syrup is treated with ethanol and n-hexane. The organic solvent layer is decanted from the deposited oil and crystallizes to give 4.8 g. of the product of the Example as bright yellow plates, m.p. 82°–83° C.

EXAMPLE 19

N'-[2,6-Dichloro-4-[(p-dimethylaminobenzylidene)-amino)phenyl]-N,N-dimethylformamidine An 8.85 g. amount of recrystallized 2,6-dichloro-p-phenylenediamine is dissolved in 50 ml. of refluxing ethanol, then 7.41 g. of p-dimethylaminobenzaldehyde is added and the mixture is refluxed for 3 hours. The mixture is cooled and n-hexane is added until turbid. The mixture is stored at 5° C. for 16 hours. The crude product is collected by filtration and washed with n-hexane. The product is recrystallized from 50 ml. of ethanol, filtered and washed with ether to give 10.4 g. of 2,6-dichloro-$N^4$-(p-dimethylaminobenzylidene)-p-phenylenediamine as granular yellow crystals, m.p. 127°–128° C.

A 3.0 g. amount of the preceding compound in 15 ml. of N,N-dimethylformamide dimethylacetal is refluxed for 18 hours. The solution is evaporated in vacuo to give a syrup. The syrup is dissolved in 25 ml. of refluxing ethanol and filtered. The filtrate is cooled to precipitate the product which is collected and washed with ethanol followed by n-hexane to give 3.3 g. of the product of the Example as bright yellow plates, m.p. 132°–134° C.

EXAMPLE 20

N'-[2,6-Dichloro-4-[(4-dimethylamino-2-methoxybenzylidene)amino)phenyl]-N,N-dimethylformamidine An 8.0 g. amount of recrystallized 2,6-dichloro-p-phenylenediamine is dissolved in 50 ml. of warm ethanol then 8.1 g. of 4-dimethylamino-2-methoxybenzaldehyde is added and the mixture is heated at the reflux temperature for 5 hours. The solution is cooled to room temperature and crystallization is induced by the addition of several drops of n-hexane. Filtration gives 9.2 g. of 2,6-dichloro-$N^4$-(4-dimethylamino-2-methoxybenzylidene)-p-phenylenediamine as bright yellow crystals, m.p. 137°–139° C.

A 3.0 g. amount of the above compound in 15 ml. of N,N-dimethylformamide dimethylacetal is heated at reflux temperature for 6 hours. The mixture is evaporated to an amber colored syrup which is dissolved in 25 ml. of hot ethanol. The mixture is cooled to room temperature, then diluted to 200 ml. with n-hexane. Cooling at 5° C. gives 1.3 g. of the product of the Example, m.p. 111°–116° C.

EXAMPLE 21

4'-[N-[3,6-Dichloro-4-[(dimethylaminomethyleneamino)-phenyl]formimidoyl]-3,4,5-trimethoxybenzanilide A 4.42 g. amount of recrystallized 2,6-dichloro-p-phenylenediamine is dissolved in 50 ml. of refluxing ethanol and 7.88 g. of 4'-formyl-3,4,5-trimethoxybenzanilide is added. An additional 25 ml. of ethanol is added, the mixture is refluxed for 2 hours, then is cooled to yield a precipitate. The product is filtered and washed with n-hexane to give 9.0 g. of 4'-[N-(4-amino-3,5-dichlorophenyl)formimidoyl]-3,4,5-trimethoxybenzanilide as pale yellow needles, m.p. 204°–206° C.

A 1.0 g. amount of the above compound is suspended in 75 ml. of dichloromethane and 5 ml. of N,N-dimethylformamide dimethylacetal. The mixture is stirred at room temperature for 16 hours then is filtered. The pale yellow cake (800 mg.) is washed with dichloromethane. To the cake is added 5 ml. of N,N-dimethylformamide dimethylacetal and 5 ml. of dimethylformamide. The solution is allowed to stand at room temperature for 24 hours then is evaporated to a syrup. Ethanol is added to crystallize a product. The product is collected (550 mg.) and washed with ethanol. This material is refluxed for 3 hours in 25 ml. of tetrahydrofuran and N,N-dimethylformamide dimethylacetal and allowed to stand at room temperature. The solution is evaporated to dryness in vacuo. The residue is dissolved in tetrahydrofuran then 5 ml. of N,N-dimethylformamide dimethylacetal is added and the mixture is refluxed for 18 hours. The reaction mixture is evaporated to a syrup which is dissolved in chloroform and again evaporated to a syrup. The syrup is dissolved in ethanol and n-hexane is added until turbid. The solution is cooled to provide the product. The product is collected and washed with n-hexane to yield 650 mg. of the desired product as yellow crystals, m.p. 80° C.

EXAMPLE 22

N'-[2,6-Dichloro-4-[(4-diethylaminosalicylidene)-amino]phenyl]-N,N-dimethylformamidine An 8.3 g. amount of m-diethylaminophenol is formylated with Vilsmeier reagent (N,N-dimethylformamide-phosphorus oxychloride) to give 6.6 g. of 4-diethylaminosalyicylaldehyde as a purple solid, m.p. 62°–64° C.

A mixture of 3.8 g. of the preceding compound, 3.5 g. of recrystallized 2,6-dichloro-p-phenylenediamine and 50 ml. of toluene is refluxed with a Dean-Stark trap, and with several crystals, of p-toluenesulfonic acid added. The reaction mixture is filtered, the filtrate is heated with activated carbon and filtered. The filter is washed with ethanol and the combined filtrate and wash is evaporated to give a dark syrup. Ethanol is added and crystallization occurs. The mixture is cooled, filtered and washed with n-hexane to give 5.2 g. of 2-[N-(4-amino-3,5-dichlorophenyl)formimidoyl]-5-diethylaminophenol as dark golden crystals, m.p. 136°–137° C.

A 2.0 g. amount of the above compound in 15 ml. of N,N-dimethylformamide dimethylacetal is refluxed for 8 hours. The reaction mixture is evaporated to a syrup. The syrup is dissolved in 20 ml. warm ethanol and n-hexane is added to a volume of 500 ml. The solution is cooled at 5° C. for 16 hours to give a precipitate. The product is collected to give 1.7 g. of the product of the Example as orange needles, m.p. 123°–125° C.

EXAMPLE 23

N'-[2,6-Dichloro-4-[(4-dimethylaminosalicylidene)-amino]phenyl]-N,N-dimethylformamidine A 13.7 g. amount of 3-dimethylaminophenol is formylated with Vilsmeier reagent (N,N-dimethylformamide-phosphorus oxychloride) to give 6.6 g. of 4-dimethylaminosalicylaldehyde as brown plates, m.p. 81°–83° C.

A mixture of 6.0 g. of the preceding compound, 6.4 g. of recrystallized 2,6-dichloro-p-phenylenediamine and 100 ml. of absolute ethanol is refluxed for 4 hours. The reaction mixture is cooled at 5° C. for 16 hours to precipitate a product. The product is collected, washed with ethanol/n-hexane then n-hexane to yield 9.0 g. of 2-[N-(4-amino-3,5-dichlorophenyl)formimidoyl]-5-dimethylaminophenol as golden-yellow, granular crystals, m.p. 166°–167° C.

A 1.5 g. amount of the preceding compound and 10 ml. of N,N-dimethylformamide dimethylacetal is refluxed for 5 hours. The reaction mixture is allowed to stand at room temperature for 16 hours. The mixture is evaporated in vacuo. The residue is recrystallized from ethanol and the product is collected and washed with ethanol/n-hexane, then hexane to give 1.6 g. of the product of the Example as golden plates, m.p. 140°–141° C.

EXAMPLE 24

N'-[4-(3-Bromo-4-dimethylaminobenzylideneamino]-2,6-dichlorophenyl]-N,N-dimethylformamidine An 8.8 g. amount of recrystallized 2,6-dichloro-p-phenylenediamine is dissolved in 40 ml. of ethanol by refluxing, then 11.4 g. of 3-bromo-4-dimethylaminobenzaldehyde [prepared by the method of Brady and Truszkowske, J. Chem. Soc., 123, 2438 (1923)] in 10 ml. of ethanol is added. The mixture is refluxed for 6 hours, then cooled to separate an oil. The oil gradually crystallizes to a solid. This material is filtered and washed with n-hexane until the wash is clear to give 17.3 g. of $N^4$-(3-bromo-4-dimethylaminobenzylidene)-2,6-dichloro-p-phenylenediamine as pale yellow crystals, m.p. 138°–140° C.

A 3.7 g. amount of the preceding compound in 15 ml. of N,N-dimethylformamide dimethylacetal is heated at reflux for 6 hours. The volatiles are evaporated *in vacuo* to give a dark syrup. The product is crystallized from ethanol, filtered and washed with ethanol, then hexane to provide 3.7 g. of the desired product as golden crystals, m.p. 140°–141° C.

EXAMPLE 25

N'-[2,6-Dichloro-4-(p-dimethylaminocinnamylidene)-amino)phenyl]-N,N-dimethylformamidine An 8.8 g. amount of recrystallized 2,6-dichloro-p-phenylenediamine is dissolved in 50 ml. of ethanol and 8.75 g. of p-dimethylaminocinnamaldehyde is added. The mixture is refluxed for 2 hours and cooled. Ethanol is added to separate the product which is collected and washed with ethanol, ethanol/n-hexane and n-hexane to give 15.0 g. of 2,6-dichloro-$N^4$-(p-dimethylaminocinnanylidene)-p-phenylenediamine as orange crystals, m.p. 173°–175° C.

A mixture of 4.0 g. of the above product, 15 ml. of N,N-dimethylformamide dimethylacetal and 50 ml. of tetrahydrofuran is refluxed for 8 hours. The reaction solution is evaporated to a syrup, ethanol is added and the syrup is dissolved by refluxing. The mixture is cooled and n-hexane is added to crystallize a product. The material is collected and washed with n-hexane to give 2.8 g. of dark yellow crystals. The crude product is recrystallized from boiling ethanol, washed with ethanol, then n-hexane and dried over phosphorus pentoxide to give 1.7 g. of dark yellow crystals.

A slurry of 150 g. of silica gel in chloroform is packed in a chromatographic column and the above material (1.7 g.), dissolved in chloroform, is added to the column. The column is eluted with chloroform:methanol (20:1). The column chromatography is monitored by thin later chromatography (tlc) [using chloroform:methanol (20:1) to develop the (tlc) plates] to collect 2 separate fractions. The second fraction is evaporated to a dark syrup. The syrup is treated with ethanol/n-hexane to crystallize 610 mg. of the product of the Example as rosettes, m.p. 134°–137° C. (dec.).

EXAMPLE 26

N'-[2,6-Dichloro-4-[(4-dimethylamino-2-methylbenzylidene)amino]phenyl]-N,N-dimethylformamidine A 25.0 g. amount of N,N-dimethyl-m-toluidine is formylated with Vilsmeier reagent (N,N-dimethylformamide-phosphorus oxychloride) to give 19.0 g. of 4-dimethylamino-o-tolualdehyde as pale yellow crystals, m.p. 64°–65° C. A 10.6 g. amount of recrystallized 2,6-dichloro-p-phenylenediamine is dissolved in 50 ml. of warm ethanol, then 9.8 g. of 4-dimethylamino-o-tolualdehyde is added and the mixture is heated at a simmer for 3 hours. The mixture is allowed to stand at room temperature for 16 hours, then is evaporated to dryness. The residue is recrystallized from ethanol/n-hexane, filtered and washed with ethanol/hexane to yield 12.0 g. of 2,6-dichloro-$N^4$-(4-dimethylamino-2-methylbenzylidene)-p-phenylenediamine as mustard colored needles, m.p. 92°–93° C.

A 2.0 g. amount of the above compound in 10 ml. of N,N-dimethylformamide dimethylacetal is refluxed for 7 hours. The mixture is evaporated in vacuo to a syrup. The syrup is dissolved in ethanol and n-hexane is added until turbid. A portion is decanted and yellow crystals form in the supernatant. The mixture is cooled at 5° C.

The product is collected and washed with ether/hexane to yield 2.0 g. of the product of the Example as dark yellow granules, m.p. 134°–136° C.

EXAMPLE 27

N'-[4-[(2-Bromo-4-dimethylaminobenzylideneamino]-2,6-dichlorophenyl]-N,N-dimethylformamidine A 31.0 g. amount of 3-bromo-dimethylaniline and 20 ml. of dry N,N-dimethylformamide is added over a 20 minute period to a cold stirred solution of Vilsmeier reagent (N,N-dimethylformamide-phosphorus oxychloride) to give 28.5 g. of pale yellow crystals. The product is recrystallized from hexane, filtered and washed with hexane to give 20.3 g. of 2-bromo-4-dimethylaminobenzaldehyde as colorless needles, m.p. 86°–88° C.

A 10.6 g. amount of 2,6-dichloro-p-phenylenediamine is dissolved in 50 ml. of warm ethanol and 13.7 g. of the preceding aldehyde is added. The reaction mixture is refluxed for one hour then is allowed to stand at room temperature. The solid is collected by filtration and washed with ethanol/hexane, then hexane to yield 21 g. of N$^4$-(2-bromo-4-dimethylaminobenzylidene)-2,6-dichloro-p-phenylenediamine as mustard colored crystals, m.p. 152°–153° C.

A 7.0 g. amount of the above compound in 15 ml. of N,N-dimethylformamide dimethylacetal is refluxed for 18 hours. The product is crystallized from 100 ml. of ethanol and is collected to give 3.6 g. of the product of the Example as dark golden plates, m.p. 147°–148° C.

EXAMPLE 28

N'-[2,6-Dichloro-4-[(4-dimethylamino-2-fluorobenzylidene)-amino)phenyl-N,N-dimethylformamidine An 8.8 g. amount of 2,6-dichloro-p-phenylenediamine is dissolved in 100 ml. of refluxing ethanol. Then 8.4 g. of 4-dimethylamino-2-fluorobenzaldehyde [prepared by the method of J. Org. Chem., 25, 2053 (1960)] is added, the mixture is refluxed for 4 hours, cooled, filtered and washed with cold ethanol, ethanol-hexane then hexane to give 12.0 g. of 2,6-dichloro-N$^4$-(4-dimethylamino-2-fluorobenzylidene)-p-phenylenediamine as crystals, m.p. 127°–128° C.

A 10.0 g. amount of the preceding compound in 35 ml. of N,N-dimethylformamide dimethylacetal is refluxed for 18 hours. The reaction mixture is evaporated in vacuo to give bright yellow crystals. The product is recrystallized from ethanol to give 10.2 g. of the product of the Example, m.p. 145°–146° C.

EXAMPLE 29

N'-[2,6-Dichloro-4-[(2-chloro-4-methoxybenzylidene)-amino]phenyl]-N,N-dimethylformamidine A 15.1 g. amount of 2,6-dichlorophenylenediamine and 14.5 g. of 2-chloro-4-methoxybenzaldehyde is dissolved in 200 ml. of warm ethanol. After heating at the reflux temperature for 30 minutes the mixture is cooled to room temperature and the product filtered off. Recrystallization from ethanol gives 1.7 g. of 2,6-dichloro-N$^4$-(2-chloro-4-methoxybenzylidene)-p-phenylenediamine as yellow crystals, m.p. 161°–162° C.

A 1.0 g. amount of the above material in 5 ml. of N,N-dimethylformamide diethylacetal is heated at the reflux temperature for 18 hours. The residue is dissolved in methylene chloride and passed through hydrous magnesium silicate. Addition of n-hexane to the effluent gives 850 mg. of the product of the Example as yellow plates, m.p. 129°–129.5° C.

We claim:

1. A compound selected from the group consisting of those of the formula:

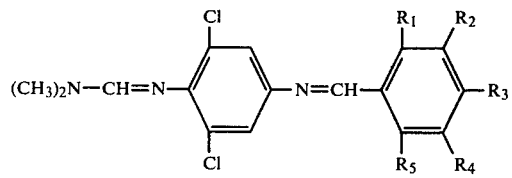

wherein $R_1$, $R_2$, $R_4$ and $R_5$ are each individually selected from the group consisting of hydrogen, fluoro, chloro, bromo, hydroxy, methoxy, methyl and trifluoromethyl; $R_3$ is selected from the group consisting of hydrogen, fluoro, chloro, bromo, cyano, hydroxy, methoxy, methyl, trifluoromethyl, phenyl, acetamido, dimethylamino and diethylamino; and $R_2$ and $R_3$ taken together is methylenedioxy with the proviso that at least two of $R_1$, $R_2$, $R_3$, $R_4$ and $R_5$ are hydrogen; and the pharmacologically acceptable acid-addition salts thereof.

2. The compound according to claim 1 wherein $R_1$ and $R_5$ are both chloro and $R_2$, $R_3$ and $R_4$ are all hydrogen; N'-[2,6-dichloro-4-(2,6-dichlorobenzylideneamino)phenyl]-N,N-dimethylformamidine.

3. The compound according to claim 1 wherein $R_1$ is chloro, $R_3$ is dimethylamino and $R_2$, $R_4$ and $R_5$ are all hydrogen; N'-[2,6-dichloro-4-[(2-chloro-4-dimethylaminobenzylideneamino]phenyl]-N,N-dimethylformamidine.

4. The compound according to claim 1 wherein $R_2$ and $R_4$ are both methoxy and $R_1$, $R_3$ and $R_5$ are all hydrogen; N'-[2,6-dichloro-4-(3,5-dimethoxybenzylideneamino)phenyl]-N,N-dimethylformamidine.

5. The compound according to claim 1 wherein $R_3$ is cyano and $R_1$, $R_2$, $R_4$ and $R_5$ are all hydrogen; N'-[2,6-dichloro-4-(p-cyanobenzylideneamino)phenyl]-N,N-dimethylformamidine.

6. The compound according to claim 1 wherein $R_2$ and $R_3$ together are methylenedioxy and $R_1$, $R_4$ and $R_5$ are all hydrogen; N'-(2,6-dichloro-4-piperonylideneaminophenyl)-N,N-dimethylformamidine.

7. The compound according to claim 1 wherein $R_1$ is fluoro and $R_2$, $R_3$, $R_4$ and $R_5$ are all hydrogen; N'-[2,6-dichloro-4-(o-fluorobenzylideneamino)phenyl]-N,N-dimethylformamidine.

8. The compound according to claim 1 wherein $R_3$ is phenyl and $R_1$, $R_2$, $R_4$ and $R_5$ are all hydrogen; N'-[2,6-dichloro-4-(p-phenylbenzylideneamino)phenyl]-N,N-dimethylformamidine.

9. The compound according to claim 1 wherein $R_1$ is methoxy, $R_3$ is dimethylamino and $R_2$, $R_4$ and $R_5$ are all hydrogen; N'-[2,6-dichloro-4-(4-dimethylamino-2-methoxybenzylideneamino)phenyl]-N,N-dimethylformamdine.

10. The compound according to claim 1 wherein $R_3$ is acetamido and $R_1$, $R_2$, $R_4$ and $R_5$ are all hydrogen; 4'-[N-[3,5-dichloro-4-(dimethylaminomethyleneamino)]phenylformimidoyl]acetanilide.

11. A compound selected from the group consisting of 4'-[N-[3,6-dichloro-4-(dimethylaminomethyleneamino)phenyl]formimidoyl]-3,4,5-trimethoxybenzanilide and the pharmacologically acceptable acid-addition salts thereof.

12. A compound selected from the group consisting of N'-[2,6-dichloro-4-[(p-dimethylaminocinnamylideneamino)phenyl]-N,N-dimethylformamidine and the pharmacologically acceptable acid-addition salts thereof.

* * * * *